United States Patent [19]

King

[11] Patent Number: 4,473,562

[45] Date of Patent: Sep. 25, 1984

[54] PESTICIDAL O-(N-ALKOXY-ALIPHATIC HYDROXAMATE)-PHOSPHORUS ESTERS AND THIOESTERS

[75] Inventor: William F. King, Novato, Calif.

[73] Assignee: Chevron Research Company, San Francisco, Calif.

[21] Appl. No.: 411,757

[22] Filed: Aug. 26, 1982

[51] Int. Cl.³ ................... C07F 9/09; C07F 9/40; A01N 57/12

[52] U.S. Cl. ....................... 424/211; 260/944

[58] Field of Search .................. 260/944; 424/211

[56] References Cited

U.S. PATENT DOCUMENTS

| | | | |
|---|---|---|---|
| 3,760,041 | 9/1973 | Lorenz et al. | 424/211 |
| 3,769,419 | 10/1973 | Gutman | 424/211 |
| 3,792,130 | 2/1974 | Stach | 424/211 |
| 3,872,185 | 3/1975 | Lorenz et al. | 424/211 |
| 4,054,650 | 10/1977 | Lorenz et al. | 424/211 |
| 4,076,808 | 2/1978 | Lorenz et al. | 424/211 |

OTHER PUBLICATIONS

Hokko et al., "Chem. Abst.", vol. 99, (1983), abstract of Japanese Kokai 83, 39, 692.

Primary Examiner—Anton H. Sutto
Attorney, Agent, or Firm—S. R. LaPaglia; T. G. DeJonghe; S. L. Biggs

[57] ABSTRACT

O-(N-alkoxy-aliphatic hydroxamate)-phosphorus esters and thioesters of the formula:

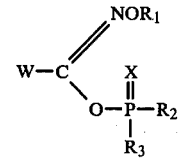

wherein W is lower alkyl, lower cycloalkyl, lower aralkyl optionally substituted with 1 or 2 halogens, lower alkenyl, trihalomethyl or lower haloalkenyl; X is sulfur or oxygen; $R_1$ is lower alkyl, lower alkenyl, lower haloalkenyl, lower alkynyl or benzyl optionally substituted with 1 to 3 halogens; $R_2$ is lower alkyl, lower alkoxy or lower alkylthio; and $R_3$ is lower alkoxy, lower alkylthio, lower alkylamino or phenyl, provided that when W is trihalomethyl, $R_3$ is not lower alkoxy, exhibit insecticidal activity.

27 Claims, No Drawings

PESTICIDAL O-(N-ALKOXY-ALIPHATIC HYDROXAMATE)-PHOSPHORUS ESTERS AND THIOESTERS

BACKGROUND OF THE INVENTION

This invention relates to certain novel O-(N-alkoxy-aliphatic hydroxamate)-phosphorus esters and thio esters and their use as insecticides. These compounds are very effective in killing a wide variety of insects.

U.S. Pat. No. 3,760,041 discloses insecticidal and acaricidal compounds of the general formula:

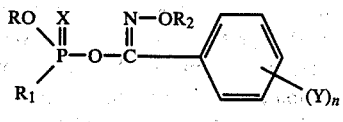

in which
R and $R_2$ each is an alkyl radical of 1 to 6 carbon atoms,
$R_1$ is an alkyl or alkoxy radical of 1 to 6 carbon atoms,
X is an oxygen or sulfur atom,
n is an integer from 0 to 5, and
Y is a halogen atom, an alkyl radical to 1 to 4 carbon atoms or a nitro group.

U.S. Pat. No. 3,872,185 discloses insecticidal and acaricidal compounds of the general formula:

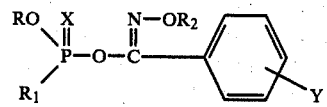

in which
R and $R_2$ each independently is alkyl of 1 to 6 carbon atoms,
$R_1$ is alkyl or alkoxy of 1 to 6 carbon atoms,
X is oxygen or sulfur, and Y is lower alkoxy or alkylmercapto.

U.S. Pat. No. 4,076,808 discloses insecticidal and acaricidal compounds of the general formula:

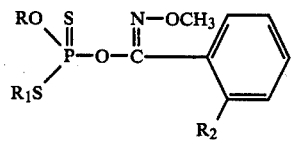

in which
R and $R_1$ each independently is alkyl with 1 to 4 carbon atoms, and
$R_2$ is hydrogen or nitro.

Preferably R is ethyl and $R_1$ is alkyl with 3 or 4 carbon atoms.

U.S. Pat. No. 4,054,650 discloses a compound of the formula:

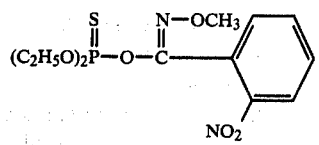

which possesses arthropodicidal properties.

U.S. Pat. No. 4,327,089 discloses a group of insecticidal and acaricidal compounds having the general formula:

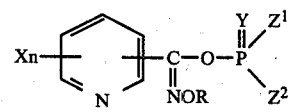

wherein X is halogen, lower alkyl, lower acyloxy, trifluoromethyl or nitro; n is 0, 1, 2 or 3, Y is O or S; R is lower alkyl; and $Z^1$ and $Z^2$ are each lower alkoxy, lower alkylthio, phenyl optionally substituted with lower alkyl phenoxy, haloalkoxy or alkylamino.

SUMMARY OF THE INVENTION

The pesticidal O-(N-alkoxy-aliphatic)-phosphorus esters and thio-esters of this invention ae represented by the formula:

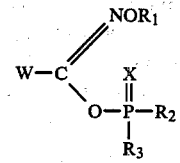

wherein W is lower alkyl, lower cycloalkyl, lower aralkyl optionally substituted with 1 or 2 halogens, lower alkenyl, trihalomethyl or lower haloalkenyl; X is sulfur or oxygen; $R_1$ is lower alkyl, lower alkenyl, lower haloalkenyl, lower alkynyl or benzyl optionally substituted with 1 to 3 halogens; $R_2$ is lower alkyl, lower alkoxy or lower alkylthio; and $R_3$ is lower alkoxy, lower alkylthio, lower alkylamino, or phenyl; provided that when W is trihalomethyl, $R_3$ is not lower alkoxy.

Among other factors, the present invention is based upon my finding that these O-(N-alkoxy-aliphatic)-phosphorus compounds exhibit surprisingly good activity as insecticides and are effective in killing a wide variety of insects.

Preferred compounds include those where $R_1$ is lower alkyl, $R_2$ is lower alkyl or lower alkoxy, $R_3$ is lower alkoxy, and W is lower aralkyl or cyclopropyl.

DEFINITIONS

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, and the like.

The term "cycloalkyl" refers to cyclic alkyl groups. The term "lower cycloalkyl" refers to cyclic alkyl groups having a total of from 3 to 8 carbon atoms. Typical lower cycloalkyls include cyclopropyl, cyclopentyl, cyclohexyl and the like.

The term "alkenyl" refers to unsaturated alkyl groups having a double bond (e.g., $CH_3CH=CHCH_2CH_2-$) and includes both straight- and branched-chain alkenyl groups. "Lower alkenyl" refers to groups having a total of from 2 to 6 carbon atoms. Typical lower alkenyl groups include, for example, propenyl, but-3-enyl, pent-4-enyl, and the like.

The term "halo" or "halogen" refers to the groups fluoro, chloro, bromo and iodo.

The term "haloalkenyl" refers to alkenyl groups substituted with from 1 halogen to complete replacement of hydrogen with halogen. "Lower haloalkenyl" refers to groups having a total of from 2 to 6 carbon atoms and includes, for example, 1-chloro-propenyl, 2,3-dibromo-but-3-enyl, and the like.

The term "alkynyl" refers to unsaturated alkyl groups having a triple bond (e.g., $CH_3C{\equiv}CCH_2CH_2—$) and includes both straight- and branched-chain alkynyl groups. "Lower alkynyl" refers to groups having a total of from 2 to 6 carbon atoms. Typical lower alkynyl groups include propynyl, butynyl, pentynyl, and the like.

The term "alkoxy" refers to the group $R'O—$ wherein $R'$ is alkyl. The term "lower alkoxy" refers to alkoxy groups having from 1 to 3 carbon atoms; examples include methoxy, ethoxy, isopropoxy, and the like.

The term "alkylthio" refers to the group $R'S—$ wherein $R'$ is alkyl. The term "lower alkylthio" refers to alkylthio groups having 1 to 3 carbon atoms; examples include methylthio, ethylthio, isopropylthio, and the like.

The term "alkylamino" refers to the group $R'R''N—$ wherein $R'$ is alkyl and $R''$ is hydrogen or alkyl. The term "lower alkylamino" refers to alkylamino groups having 1 to 6 carbon atoms. Typical alkylamino groups include methylamino, ethylamino, diethylamino, dimethylamino, and the like.

The term "alkylene" refers to the group $—(CH_2)_x—$ wherein x is an integer one or greater, and includes, for example, methylene, ethylene, propylene and the like.

The term "aryl" refers to aryl groups having from 6 to 10 carbon atoms and includes both substituted and unsubstituted aryl groups. Typical aryl groups include phenyl, p-chlorophenyl, m-methylphenyl, p-butylphenyl, and m-trifluoromethylphenyl.

The term "aralkyl" refers to an alkyl group of 1 to 4 carbons substituted with an aryl group of from 6 to 10 carbons and includes, for example, benzyl, p-chlorobenzyl, p-methylbenzyl and 2-phenylethyl.

The terms "insecticide" and "insect" as used herein refer to their broad and commonly understood usages rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs such as spiders, mites, ticks, centipedes, worms, and the like.

DETAILED DESCRIPTION OF THE INVENTION

The compounds of this invention (I) may be prepared by subjecting the appropriate N-alkoxy-aliphatichydroxamic acid derivative (II) to a phosphorylation reaction:

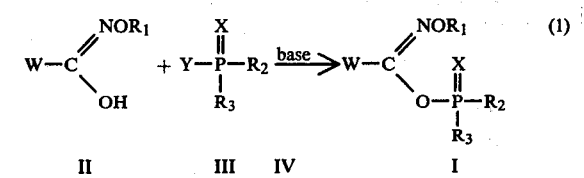

wherein W, X, $R_1$, $R_2$ and $R_3$ are as defined in conjunction with formula I and Y is halogen. The phosphorus reagents have general formula III.

Reaction (1), the phosphorylation reaction is carried out in an inert organic solvent such as methyl ethyl ketone, dimethoxyethane, acetone, acetonitrile, ether, methanol, benzene or toluene. Although approximately equimolar amounts of II, III and IV may be used, it is preferred to have a slight excess of III and IV which results in better yields and easier workups of the products. Either II or III may be added to the other in the solvent; however, it is preferred to add the phosphorus reagent dissolved in a small amount of solvent to a solution of II and IV. The addition is carried out at temperatures in the range of about 0° C. to about 35° C. Upon completion of the addition of III, the temperature of the reaction mixture is raised, preferably to reflux (about 60° C.), and the mixture stirred at reflux until the reaction is complete, about 4 to about 36 hours. At completion of the reaction, the solvent is stripped under reduced pressure and heat. The product I is then isolated by conventional procedures such as extraction, chromatography and filtration.

The preferred base IV is potassium carbonate; other suitable bases include sodium hydride and sodium metal.

The reagents, II, used in the phosphorylation reaction may be prepared according to the following reaction schemes:

(a) where $R_3$ is lower alkoxy or lower alkylthio or phenyl, phosphorus reagent III may be prepared as follows:

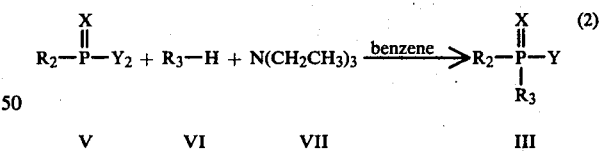

where $R_2$, $R_3$, X and Y are as defined in conjunction with reaction (1) and formula I.

Reaction (2) is carried out by adding an approximately equimolar amount of VI to a stirred solution of V in benzene. An approximately equimolar amount of VII is slowly added in a dropwise amount over a period from about 0.5 to 1 hour. After the addition is complete, the reaction mixture is stirred for an extended period of time, about 16 hours, filtered and the solvent stripped. Other inert organic solvents such as toluene may be used in place of benzene.

(b) where $R_3$ is alkylamino, represented by $—NR_5R_6$, phosphorus reagent III may be prepared according to the following reaction scheme:

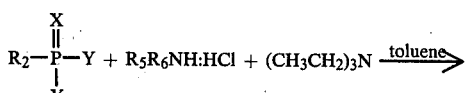

VIII     IX     X     XI

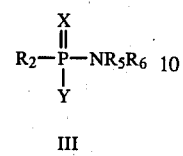

III wherein X, $R_2$, $R_3$, and Y are as defined in conjunction with formula I and reaction (1), and $R_3$ is represented by $-NR_5R_6$ where $R_5$ is alkyl and $R_6$ is hydrogen or alkyl.

Reaction (3) is carried out by the addition of X to a stirred mixture of VIII and IX in XI. It is preferred that the addition be made slowly, preferably in a dropwise manner. Since the addition reaction is exothermic, it is preferred that the reaction vessel be cooled during the addition, such as by use of an ice-water bath. Once the reaction is complete, the solvent is stripped. The crude product, III may then be purified by conventional procedures such as washing, extraction, and fast chromatography. Besides toluene other suitable solvents include benzene.

Some phosphorus reagents III, such as those where $R_2$ and $R_3$ are both alkoxy are commercially available.

Compound II, the hydroxamic acid derivative, used in the preparation of the compounds of this invention may be prepared according to the following reaction scheme:

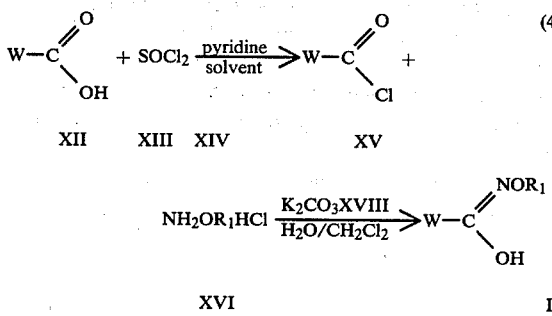

wherein W and $R_1$ are as defined in conjunction with formula I.

Reaction (4) is carried out by warming a stirred mixture of XII in solvent to about 20° to about 35° C. with a catalytic amount of pyridine XIV (about 1 ml pyridine per 0.5 mole XII). To that mixture, a solution of XIII in a small amount (about 10 ml) solvent is added dropwise; the resulting mixture is then refluxed for about 6 to about 36 hours. The solvent is stripped and product is obtained free from XIII by chasing with toluene. Product XV is immediately dissolved in solvent used in the second step of reaction (4) without further isolation. Other well-known reagents for the conversion of a carboxylic acid to the corresponding acid chloride may be used in place of thionyl chloride XIII. Although roughly equimolar amounts of XII and XIII may be used, it is preferable to use a slight excess of XIII.

A mixture of XVI and XVIII in methylene chloride/water, prepared at low temperature (less than −5° C.) is then added to the mixture of XV insolvent and the resulting mixture stirred for about 6 to 36 hours. Although roughly equimolar amounts of XV and XVI may be used, it is preferable to use a slight excess of XVI. Reaction (4) is carried out in an inert organic solvent; suitable solvents include, methylene, chloride, ether and toluene. The product II, a solid, may be isolated by conventional procedures such as stripping, extraction, chromatography, filtration and crystallization.

Alternatively, where the acid chloride XV is commercially available, intermediate II may be prepared using the acid chloride XV according to the following reaction scheme:

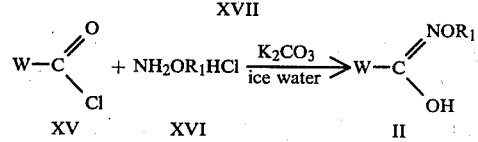

wherein $R_1$ and W are as defined in conjunction with formula I.

Reaction (5) is carried out by adding XV to a stirred mixture of XVI and XVII in ice water in drops. The resulting mixture is then stirred for about 5 to about 16 hours at room temperature. The product II a solid may then be isolated by conventional procedures such as stripping, extraction, chromatography, filtration, crystallization and the like. Although roughly equimolar amounts of XV and XVI may be used, it is preferable to use a slight excess of XVI.

UTILITY

The compounds of this invention are surprisingly effective in killing a variety of insects.

The present compounds can be stored and applied as formulations incorporated with compatible biologically inert extenders or carriers such as are typically employed for facilitating dispersion of active ingredients for agricultural chemical applications. These formulations typically contain about from 0.5 to 95 weight % of the present compound, and optionally can contain compatible insecticides, fungicides, etc., and the remainder biologically inert material including dispersing agents, emulsifying agents, wetting agents and carriers.

Such formulations can be formulated as sprays, dusts, or granules and applied to the insects and/or their environment or hosts susceptible to insect attack. They can be formulated as granules of large particle size, as powdery dusts, as wettable powders, as emulsifiable concentrates, as solutions, or as any of several other known types of formulations, depending on the desired mode of application. (Wettable powders generally refer to a form of finely divided particles which disperse readily in water or other dispersant.) Typical carriers include fuller's earth, kaolin clays, silicas, and other highly absorbent, readily wet, inorganic diluents. Typical wetting, dispersing, or emulsifying agents used in agricultural formulations include, for example, the alkyl and alkylaryl sulfonates and sulfonates and their sodium salts; alkylamide sulfonates, including fatty methane taurides, alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface active agents are available in commerce. The surface active agent, when used, normally comprises from one percent to fifteen percent by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains about 65–80 weight % silica and 35–20 weight % of the compound(s) of the invention.

Useful liquid concentrates include the emulsifiable concentrates, which are homogeneous liquid or paste compositions which are readily dispersed in water to other dispersant, and can consist entirely of the compound(s) of the invention with a liquid or solid emulsifying agent, or can also contain a liquid carrier, such as xylene, heavy aromatic naphthas, isophorone, and other non-volatile organic solvents. These concentrates are usually dispersed in water, or their liquid carrier, and then applied as a spray or paint to the area to be treated.

Other useful formulations include simple solutions of the active compound in a dispersant in which it is completely soluble at the desired concentration, such as acetone, alkylated naphthalenes, xylenes, or other organic solvents.

Optimum formulation concentrations and the manner and frequency of application may vary somewhat with the particular species of insect, the degree of infestation, the environment, including type of soil, soil conditions and weather conditions (e.g., rain fall), and can be obtained by routine experimentation.

A further understanding of my invention can be had from the following non-limiting examples.

EXAMPLE 1

Preparation of

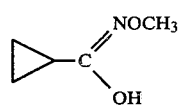

To a mixture of 69.1 g (0.5 moles) potassium carbonate in about 100 ml water, 41.8 g (0.5 moles) of methoxyamine hydrochloride ($H_2NOCH_3 \cdot HCl$) in about 20 ml water was added and the resulting mixture stirred about 20 minutes, maintaining its temperature in the range of about 0° to about 10° C. with an ice bath. To that mixture, 47 g (0.45 moles)

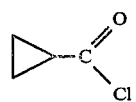

(cyclopropanecarboxylic acid chloride) was added dropwise, maintaining a reaction temperature in the range of about 0° to about 10° C. The reaction mixture was allowed to stir overnight at room temperature. The crude product was obtained from the reaction mixture by filtering. The precipitate was stirred in hexane with a small amount of diethyl ether and filtered to obtain the product, an off-white solid.

Elemental analysis for $C_5H_9NO_2$ showed: calculated % C 52.5, % H 7.88, and % N 12.2; found % C 53.6, % H 8.71, and % N 12.2.

EXAMPLE 2

Preparation of Ethyl-O-isopropylphosphonothioic chloride

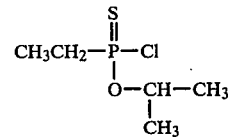

To a stirred mixture of 74.2 g (0.455 moles)

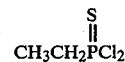

ethylphosphonothioic dichloride in 400 ml benzene, 30.1 g (0.5 moles) isopropyl alcohol was added. To that mixture 50.6 g (0.5 moles) triethylamine was added at a dropwise rate overnight. The mixture was then warmed for about 1 hour. The mixture was filtered by gravity. Most of the solvent (benzene) was stripped off under reduced pressure and heat to give ethyl-O-isopropylphosphonothioic chloride:

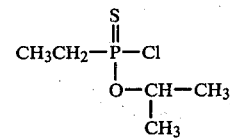

EXAMPLE 3

Preparation of Methyl-O-ethylphosphonothioic chloride

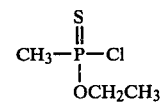

A stirred mixture of 37.3 g (0.25 moles) methylphosphonothioic dichloride and 11.5 g (0.25 moles) ethyl alcohol in about 250 ml benzene was cooled to below 0° C. in an ice/acetone bath. To that cooled mixture, 25 g (0.25 moles) triethylamine diluted with about 10 ml benzene was added dropwise. The reaction mixture was then allowed to stir at room temperature over the weekend. The reaction mixture was then heated to about 60° C. (just below the reflux temperature for benzene) for about 2 hours. The reaction mixture was filtered and washed with cold water. The phases were separated, the benzene (organic) layer extracting the product. The benzene layer was dried over magnesium sulfate, filtered and stripped to give the crude product. Chromatography on a silica gel column, eluting with hexane, gave about 9 g of the product, a colorless liquid.

EXAMPLE 4

Preparation of Ethyl-N,N-diethylaminophosphonic chloride

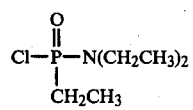

In a one-liter flask, 73.5 g (0.5 moles) of

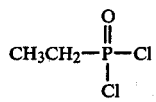

are dissolved in 300 ml toluene. To that mixture 57 g (0.52 moles), diethylamine hydrochloride [(CH$_2$CH$_3$)$_2$NH.HCl] is added with stirring. To the resulting stirred mixture, 105 g triethylamine is added in a dropwise manner. During the addition, the temperature of the reaction mixture is controlled by the use of an ice-water bath. The reaction mixture is allowed to come to room temperature, and stirred for 14 hours.

After the reaction is complete, the toluene is stripped under reduced pressure. Methylene chloride (about 300 ml) and water (about 150 ml) are added to the residue (crude product) and the mixture is stirred. The phases are separated, the product is extracted in the methylene chloride layer, and the aqueous layer is discarded. The methylene chloride layer is dried with magnesium sulfate and then filtered. The methylene chloride is then stripped to give the product.

EXAMPLE 5

Preparation of Ethyl-N,N-diethylaminophosphonothioic chloride

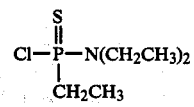

In a one-liter flask, 81.5 g (0.5 moles) of

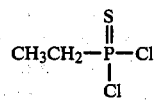

(ethylphosphonothioic dichloride)

were dissolved in 300 ml toluene. To that mixture, 57 g (0.52 moles) diethylamine hydrochloride ((CH$_3$CH$_2$)$_2$NH.HCl) was added with stirring. To the resulting stirred mixture, 105 g triethylamine was then added dropwise. During the addition, the temperature of the reaction mixture was controlled by use of an ice-water bath. The reaction mixture was allowed to come to room temperature, and stirred 14 hours.

The toluene was stripped using reduced pressure. Methylene chloride (about 300 ml) and water (about 150 ml) were added to the residue (crude product) and the mixture was stirred. The phases were separated, the product extracted in the methylene chloride (organic) phase, and the aqueous phase was discarded. The methylene chloride phase was dried with magnesium sulfate, and then filtered. The methylene chloride was then stripped to give about 90 g of product.

EXAMPLE 6

Preparation of Ethyl-S-ethylphosphonothioic chloride

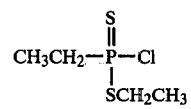

To a stirred mixture of 81.5 g (0.5 moles)

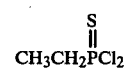

(ethylphosphonothioic dichloride), and 74 ml ethanethiol in about 400 ml benzene in a round bottom flask in an ice bath, 71 ml triethylamine was slowly added dropwise. The reaction mixture was allowed to stir at room temperature for about 24 hours. The reaction mixture was filtered and the solvent was stripped under reduced pressure and heat. Acetone (about 50 to 60 ml) was added to the residue, and the resulting mixture was stirred. The mixture was filtered to remove salts and the acetone was stripped to the crude product. Chromatography on a silica gel column eluting with hexane with 5% methylene chloride gave the product a clear light liquid.

Elemental analysis for C$_4$H$_{10}$ClPS$_2$ showed: calculated % C 25.5, % H 5.34, and % N 0; found % C 20.41, % H 5.42 and % N 0.03.

EXAMPLE 7

Preparation of O,O-Dimethyl-O-(N-methoxycyclopropane carboximidoyl)-thiophosphate

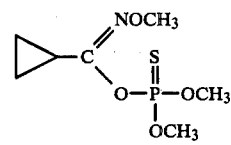

The sodium salt of the product of Example 1 was prepared by treating 3.3 g (0.029 moles) of the product of Example 1 with 0.67 g (0.029 moles) of sodium metal in about 25 ml methanol. The methanol was stripped and chased with toluene. The toluene was then stripped to give the sodium salt, which was used without further isolation.

To a mixture of 4.0 g (0.029 mole)

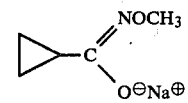

in about 25 ml hexane and 25 ml benzene, 4.66 g (0.029 moles)

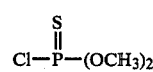

(dimethylchlorothiophosphate) in about 10 ml benzene was added dropwise. The resulting mixture was refluxed about 6 hours.

The solvent was stripped under reduced pressure and heat. Water (about 75 ml) and methylene chloride (about 75 ml) were added to the residue, and the resulting mixture stirred. The layers were separated, the methylene chloride (organic) layer extracting the product. The methylene chloride layer was washed once with a small amount of water, dried over magnesium sulfate and then filtered. Stripping of the methylene chloride gave an oil which was chromatographed on silica gel, eluting with hexane:methylene chloride (1:1) to give the product a colorless liquid.

Elemental analysis for $C_7H_{14}NO_4PS$ showed: calculated % C 35.1, % H 5.89, and % N 5.86; found % C 35.36, % H 6.14, and % N 5.84.

EXAMPLE 8

Preparation of Ethyl-O-ethyl-O-(N-methoxycyclopropanecarboximidoyl)-thiophosphonate

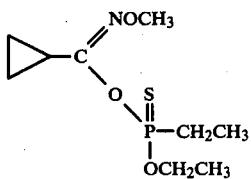

A stirred mixture of 2.9 g (0.25 moles) of the product of Example 1 and 4.2 g (0.03 moles) potassium carbonate in about 50 ml methyl ethyl ketone was warmed (to about 40° C.) for an hour. To that mixture, 5.2 g (0.03 moles) of ethyl-O-ethylphosphonothioic chloride,

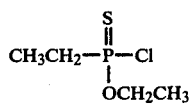

in a small amount amount (about 5 ml) methyl ethyl ketone was added dropwise. The resulting mixture was refluxed 8 hours. The methyl ethyl ketone was stripped under reduced pressure and heat. Water (about 75 ml) and methylene chloride (about 75 ml) were added to the residue, and the resulting mixture stirred. The layers were separated, the methylene chloride (organic) layer extracting the product. The methylene chloride layer was dried over magnesium sulfate and filtered, and the methylene chloride was stripped. The product was purified on a silica gel column, eluting with hexane:-methylene chloride (4:1) to yield about 4:1 g of the product, a clear liquid.

Elemental analysis for $C_9H_{18}NO_3PS$ showed: calculated % C 43.0, % H 7.22, and % N 5.57; found % C 40.2, % H 6.91, and % N 5.24.

EXAMPLE 9

Preparation of

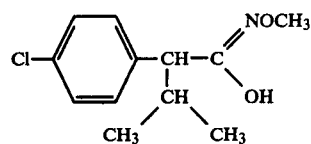

(a) A mixture 50 g (0.28 moles) of 2-(p-chlorophenyl)-3-methylbutyric acid,

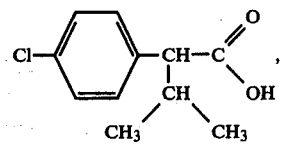

in about 300 ml methylene chloride with a catalytic amount (about 1 ml) pyridine was stirred at room temperature for about ½ hour. To that mixture 39 g (0.33 moles) thionyl chloride in about 20 ml methylene chloride was added dropwise. After the addition was complete, the reaction mixture was refluxed for about 16 hours. The methylene chloride was then removed under reduced pressure and heat. Water (about 100 ml) and fresh methylene chloride (about 200 ml) was added to the residue, the resulting mixture was stirred. The phases were separated, the methylene chloride (organic) phase extracting the product, the acid chloride. The methylene chloride layer was dried over magnesium sulfate and filtered. Stripping of the methylene chloride gave the corresponding acid chloride which was used in the second step of the reaction without further isolation.

(b) To stirred mixture of 28 g (0.33 moles) of methoxyamine hydrochloride and 17 g (0.34 moles) potassium carbonate in about 150 ml water whose temperature was maintained below 0° C., 65 g (0.28 moles) of the acid chloride of step (a) in about 150 ml methylene chloride was added dropwise. The temperature of the reaction mixture was maintained below 0° C. during the addition. After the addition was complete, the reaction mixture was stirred at room temperature for about 4 hours. The phases were separated, the methylene chloride layer extracting the product. The methylene chloride layer was dried over magnesium sulfate and filtered. Stripping of the methylene chloride gave the product, an amber viscous liquid which solidified upon standing to a light yellow solid.

EXAMPLE 10

Preparation of O,O-Diethyl-O-[(N-methoxy)-2-(p-chlorophenyl)-3-methylbutyrylcarboximidoyl]thiophosphate

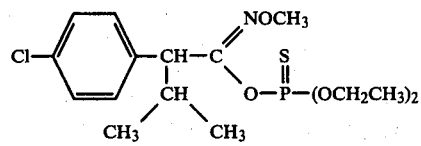

A mixture of 4.8 g (0.02 moles) of the product of Example 9 and 3.5 g (0.025 moles) potassium carbonate in about 50 ml methyl ethyl ketone was stirred together with gentle heat (about 40° C.) for an hour. To the resulting mixture 4 g (0.21 moles) of diethylchlorothiophosphonate in about 5 ml methyl ethyl ketone was added dropwise. The reaction mixture was refluxed 8 hours. The methyl ethyl ketone was removed under reduced pressure and heat. Water (about 75 ml) and methylene chloride (about 75 ml) were added to the residue; the resulting mixture was stirred. The phases were separated; the methylene chloride (organic) phase extracted the product. The methylene chloride layer was dried over magnesium sulfate and filtered. Stripping of the methylene chloride, followed by chromatography on a silica gel column, eluting with hexane:-methylene chloride (4:1) gave about 4 g of the product, a clear light yellow liquid.

Elemental analysis for $C_{16}H_{25}ClNO_4PS$ showed: calculated % C 48.8, % H 6.39, and % N 3.6; found % C 49.7, % H 6.86, and % N 4.12.

Compounds made in a manner consistent with Examples 1 to 10 are found in Table I.

EXAMPLE A

Aphid Control

Compounds of this invention were tested for their insecticidal activity against cotton aphids (Aphis gossypii Glover). An acetone solution of the test compound containing a small amount of non-ionic emulsifier was diluted with water to give a concentration of 40 ppm. Cucumber leaves infested with cotton aphids were dipped in the test compound solution. Mortality readings were taken after 24 hours. The results expressed as % control, are tabulated in Table II.

EXAMPLE B

Aphid Systemic Evaluation

This procedure is used to assess the ability of a candidate insecticide to be absorbed through the plant root system and translocate to the foliage.

Two cucumber plants planted in a 4-inch fiber pot with a soil surface area of 80 cm$^2$ are used. 40 ml of an 80 ppm solution of the candidate insecticide is poured around the plants in each pot. (This corresponds to 40 g/cm$^2$ of actual toxicant.) The plants are maintained throughout in a greenhouse at 75° to 85° F. 48 hours after the drenching, the treated plants are infested with aphids by placing well colonized leaves over the treated leaves so as to allow the aphids to migrate easily from the treated leaf. Three days after infestation, mortality readings were taken. The results are tabulated in Table II in terms of percent control.

EXAMPLE C

Mite Control

Compounds of this invention were tested for their insecticidal ability against two-spotted mites (Tetranychus urticae). An acetone solution of the test compound containing a small amount of non-ionic emulsifier was diluted with water to give a concentration of 40 ppm. Lima bean leaves which were infested with mites were dipped in the test compound solution. Mortality readings were taken after 24 hours. The results, expressed as % control, are tabulated in Table II.

EXAMPLE D

Mite Egg Control

Compounds of this invention were tested for their ovicidal activity against eggs of the two-spotted spider mite (Tetranychus urticae). An acetone solution of the test toxicant containing a small amount of non-ionic emulsifier was diluted with water to give a concentration of 40 ppm. Two days before testing, 2-week old lima bean plants were infested with spider mites. Two days after infestation, leaves from the infested plants are dipped in the toxicant solution, placed in a petri dish with filter paper and allowed to dry in the open dish at room temperature. The treated leaves were then held in covered dishes at about 31° to 33° C. for seven days. On the eighth day egg mortality readings are taken. The results, expressed as % control, are tabulated in Table II.

EXAMPLE E

Housefly

Compounds of this invention were tested for their insecticidal activity against the housefly (Musca domestica L.). A 500 ppm acetone solution of the test compound was placed in a microsprayer (atomizer). A random mixture of anesthetized male and female flies was placed in a container and 55 mg of the above-described acetone solution was sprayed on them. A lid was placed on the container. A mortality reading was then taken after 24 hours. The results are expressed as % control and are reported in Table II.

EXAMPLE F

Alfalfa Weevil

Compounds of this invention were tested for their insecticidal activity against the alfalfa weevil (H. Brunneipennis Boheman). A 500 ppm acetone solution of the test compound was placed in a microsprayer (atomizer). A random mixture of male and female weevils was placed in a container and 55 mg of the above-described acetone solution was sprayed on them. A lid was placed on the container. A mortality reading was made after 24 hours. The results are expressed as % control and are tabulated in Table II.

EXAMPLE G

American Cockroach

Compounds of this invention were tested for their insecticidal activity against the American cockroach (Periplaneta americana L.). A 500 ppm acetone solution of the test compound was placed in a microsprayer (atomizer). A random mixture of anesthetized male and female roaches was placed in a container and 55 mg of the above-described solution was sprayed on them. A lid was placed on the container. A mortality reading was made after 24 hours. The results, expressed as % control, are reported in Table II.

EXAMPLE H

Cabbage Looper

Compounds of this invention were tested for their insecticidal activity against cabbage looper (Trichoplusia ni). An acetone solution of the test compound containing a small amount of non-ionic emulsifier was diluted with water to give a concentration of 500 ppm. Excised cucumber leaves were dipped in the test compound solution and allowed to dry. The leaves were then infested with cabbage looper larvae. Mortality readings were taken after 24 hours. The results are expressed as % control and are reported in Table II.

EXAMPLE I

Control of Mosquito Larvae

The compounds of this invention were tested for control of mosquito larvae (*Aedes aegypti*). A plastic cup was filled with 90 ml deionized water and then infested with early 4th-stage mosquito larvae contained in 10 ml water. One rabbit food pellet was added to the cup to provide food for the larvae. A 200 microliter aliquot of a 500 ppm solution of the test compound was added to the cup. The water was then thoroughly mixed to give a final concentration of test compound of 0.1 ppm. The cup was covered with a plastic lid in order to prevent evaporation and to confine any subsequently emerging adult mosquitos. The cup was kept at 27° C. for 6 days at which time mortality readings were taken. The results, expressed as % control, are reported in Table II.

TABLE I

Compounds of the Formula:

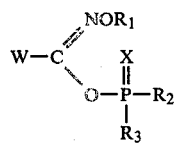

| Compound No. | W | X | $R_1$ | $R_2$ | $R_3$ | Physical State | % Carbon Calc. | % Carbon Found | % Hydrogen Calc. | % Hydrogen Found | % Nitrogen Calc. | % Nitrogen Found |
|---|---|---|---|---|---|---|---|---|---|---|---|---|
| 1 39790 | $-CH_2CH(CH_3)_2$ | S | $CH_3$ | $OCH_2CH_3$ | $OCH_2CH_3$ | colorless liquid | 42.4 | 42.5 | 7.83 | 8.56 | 4.94 | 5.3 |
| 2 39992 | $-CH_2CH(CH_3)_2$ | O | $CH_3$ | $OCH_2CH_3$ | $OCH_2CH_3$ | light amber liquid | 44.9 | 45.8 | 8.3 | 9.3 | 5.24 | 5.25 |
| 3 39859 | $-CH(CH(CH_3)_2)-C_6H_4-Cl$ | S | $CH_3$ | $OCH_2CH_3$ | $OCH_2CH_3$ | clear yellow liquid | 48.8 | 49.7 | 6.39 | 6.86 | 3.6 | 4.12 |
| 4 36245 | $-C(CH_3)=CH_2$ | S | $CH_3$ | $OCH_2CH_3$ | $OCH_2CH_3$ | yellow liquid | 40.4 | 45.8 | 6.79 | 7.36 | 5.24 | 5.02 |
| 5 35098 | cyclopropyl | S | $CH_3$ | $OCH_3$ | $OCH_3$ | colorless liquid | 35.1 | 35.36 | 5.89 | 6.14 | 5.86 | 5.84 |
| 6 34830 | cyclopropyl | S | $CH_3$ | $OCH_2CH_3$ | $OCH_2CH_3$ | yellow liquid | 40.4 | 34.2 | 6.79 | 5.89 | 5.24 | 3.65 |
| 7 39398 | cyclopropyl | O | $CH_3$ | $OCH_2CH_3$ | $OCH_2CH_3$ | clear liquid | 43 | 42.7 | 7.22 | 7.38 | 5.6 | 5.53 |
| 8 39243 | cyclopropyl | S | $CH_2CH_3$ | $OCH_2CH_3$ | $OCH_2CH_3$ | clear liquid | 42.7 | 41.0 | 7.17 | 7.33 | 4.98 | 3.99 |
| 9 39026 | cyclopropyl | S | $CH_3$ | $CH_2CH_3$ | $OCH_2CH_3$ | clear liquid | 43.0 | 40.2 | 7.22 | 6.91 | 5.57 | 5.24 |
| 10 38298 | cyclopropyl | S | $CH_3$ | $CH_2CH_3$ | $OCH(CH_3)_2$ | clear liquid | 45.3 | 44.4 | 7.6 | 7.5 | 5.28 | 5.1 |
| 11 38244 | cyclopropyl | S | $CH_2CH_3$ | $CH_2CH_3$ | $SCH(CH_3)_2$ | clear liquid | 44.7 | 42.5 | 7.51 | 7.67 | 4.74 | 3.45 |
| 12 38073 | 1-methylcyclopropyl | S | $CH_3$ | $OCH_2CH_3$ | $OCH_2CH_3$ | clear liquid | 42.7 | 38.7 | 7.17 | 6.72 | 4.98 | 3.46 |
| 13 39989 | 1-methylcyclopropyl | S | $CH_3$ | $CH_2CH_3$ | $OCH_2CH_3$ | | | | | | | |

TABLE I-continued

Compounds of the Formula:

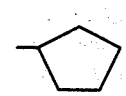

| Compound No. | W | X | R₁ | R₂ | R₃ | Physical State | %Carbon Calc. | %Carbon Found | %Hydrogen Calc. | %Hydrogen Found | %Nitrogen Calc. | %Nitrogen Found |
|---|---|---|---|---|---|---|---|---|---|---|---|---|
| 14 39591 | | S | $CH_2CH_3$ | $OCH_2CH_3$ | $OCH_2CH_3$ | pale yellow liquid | 46.6 | 44.4 | 7.82 | 7.87 | 4.53 | 3.8 |
| 15 39589 | 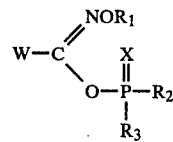 | S | $CH_2CH_3$ | $CH_2CH_3$ | $OCH_2CH_3$ | colorless liquid | 49.1 | 43.3 | 8.25 | 8.2 | 4.8 | 3.1 |
| 16 36950 | $-CCl_3$ | S | $CH_3$ | $OCH_2CH_3$ | $NHCH(CH_3)_2$ | amber liquid | 26.9 | 32.3 | 4.51 | 4.68 | 7.83 | 10.6 |
| 17 36946 | $-C{=}CCl_2$ $\vert$ $Cl$ | S | $CH_3$ | $CH_2CH_3$ | $SCH(CH_3)_3$ | colorless liquid | 29.2 | 29.9 | 4.08 | 4.45 | 3.78 | 3.42 |

TABLE II

Insecticidal Activity

| Compound No. | Aphid | Aphid Systemic | Adult Mite | Mite Egg | Housefly | Alfalfa Weevil | American Cockroach | Cabbage Looper | Mosquito Larvae |
|---|---|---|---|---|---|---|---|---|---|
| 1 39790 | 75 | 0 | 0 | 0 | 100 | 0 | 60 | 0 | 0 |
| 2 39992 | 80 | 70 | 0 | 0 | — | 0 | 75 | 0 | 0 |
| 3 39859 | 35 | 0 | 40 | 0 | 80 | 0 | 100 | 100 | 100 |
| 4 36245 | 93 | 0 | 0 | 0 | 60 | 0 | 100 | 100 | 0 |
| 5 35098 | 100 | 100 | 0 | 0 | 100 | 0 | 99 | 0 | 0 |
| 6 34830 | 99 | 0 | 39 | 0 | 100 | 0 | 100 | 80 | 100 |
| 7 38398 | 0 | 75 | 0 | 0 | 96 | 0 | 100 | 0 | — |
| 8 39243 | 100 | 0 | 0 | 0 | 93 | 0 | 100 | 10 | 70 |
| 9 39026 | 94 | 80 | 45 | 0 | 100 | — | 100 | 0 | 80 |
| 10 39298 | 99 | 0 | 0 | 0 | 100 | 0 | 99 | 0 | — |
| 11 38244 | 98 | 0 | 75 | 0 | 100 | 10 | 20 | 0 | — |
| 12 38073 | 70 | 0 | 40 | 0 | 80 | 0 | 100 | 100 | 100 |
| 13 39989 | 20 | 0 | 0 | 0 | — | 0 | 95 | 30[1] | 0 |
| 14 39591 | 0 | 0 | 0 | 0 | 20 | 0 | 0 | 0 | 0 |
| 15 39589 | 20 | 0 | 0 | 80 | 95 | 0 | 20 | 0 | 0 |
| 16 36950 | 70 | 0 | 0 | 0 | 0 | 0 | 95 | 0 | 0 |
| 17 36946 | 95 | 0 | 70 | 0 | 0 | 0 | 0 | 0 | 0 |

[1]70% at 5 days

What is claimed is:

1. A compound of the formula

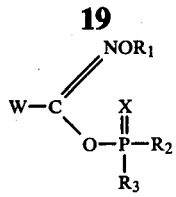

wherein X is sulfur or oxygen; $R_1$ is lower alkyl; $R_2$ is lower alkyl, lower alkoxy or lower alkylthio; $R_3$ is lower alkoxy, lower alkylthio, lower alkylamino or phenyl; and W is lower alkyl, lower cycloalkyl, lower aralkyl, optionally substituted with 1 or 2 halogens, lower alkenyl, trihalomethyl or lower haloalkenyl, provided that when W is trihalomethyl, $R_3$ is not lower alkoxy.

2. A compound according to claim 1 wherein $R_2$ is alkyl or alkoxy; and $R_3$ is alkoxy or alkylthio.

3. A compound according to claim 2 wherein W is cycloalkyl.

4. A compound according to claim 3 wherein W is cyclopropyl.

5. A compound according to claim 4 wherein X is sulfur and $R_1$ is methyl, and $R_2$ and $R_3$ are both methoxy.

6. A compound according to claim 3 wherein W is 1-methyl-cyclopropyl.

7. A compound according to claim 6 wherein X is sulfur, $R_1$ is methyl, and $R_2$ and $R_3$ are ethoxy.

8. A compound according to claim 2 wherein W is lower alkenyl.

9. A compound according to claim 8 wherein X is sulfur, W is 1-methylvinyl, $R_1$ is methyl and $R_2$ and $R_3$ are both ethoxy.

10. A method of killing insects which comprises contacting said insect or its environment with an insecticidally effective amount of a compound of claim 1.

11. A method of killing insects which comprises contacting said insect or its environment with an insecticidally effective amount of a compound of claim 2.

12. A method of killing insects which comprises contacting said insect or its environment with an insecticidally effective amount of a compound of claim 3.

13. A method of killing insects which comprises contacting said insect or its environment with an insecticidally effective amount of a compound of claim 4.

14. A method of killing insects which comprises contacting said insect or its environment with an insecticidally effective amount of a compound of claim 5.

15. A method of killing insects which comprises contacting said insect or its environment with an insecticidally effective amount of a compound of claim 6.

16. A method of killing insects which comprises contacting said insect or its environment with an insecticidally effective amount of a compound of claim 7.

17. A method of killing insects which comprises contacting said insect or its environment with an insecticidally effective amount of a compound of claim 8.

18. A method of killing insects which comprises contacting said insect or its environment with an insecticidally effective amount of a compound of claim 9.

19. An insecticidal composition comprising a biologically inert carrier and an insecticidally effective amount of a compound of claim 1.

20. An insecticidal composition comprising a biologically inert carrier and an insecticidally effective amount of a compound of claim 2.

21. An insecticidal composition comprising a biologically inert carrier and an insecticidally effective amount of a compound of claim 3.

22. An insecticidal composition comprising a biologically inert carrier and an insecticidally effective amount of a compound of claim 4.

23. An insecticidal composition comprising a biologically inert carrier and an insecticidally effective amount of a compound of claim 5.

24. An insecticidal composition comprising a biologically inert carrier and an insecticidally effective amount of a compound of claim 6.

25. An insecticidal composition comprising a biologically inert carrier and an insecticidally effective amount of a compound of claim 7.

26. An insecticidal composition comprising a biologically inert carrier and an insecticidally effective amount of a compound of claim 8.

27. An insecticidal composition comprising a biologically inert carrier and an insecticidally effective amount of a compound of claim 9.

* * * * *